(12) United States Patent
Lee et al.

(10) Patent No.: US 9,907,878 B2
(45) Date of Patent: Mar. 6, 2018

(54) **WET TISSUE CONTAINING HOT WATER EXTRACT OF *COPTIDIS RHIZOMA* EXTRACTED UNDER HIGH TEMPERATURE AND HIGH PRESSURE CONDITIONS**

(71) Applicants: Yea Sung Lee, Gyeonggi-do (KR); Yeon Ju Yu, Gyeonggi-do (KR)

(72) Inventors: Yea Sung Lee, Gyeonggi-do (KR); Yeon Ju Yu, Gyeonggi-do (KR)

( * ) Notice: Subject to any disclaimer, the term of this patent is extended or adjusted under 35 U.S.C. 154(b) by 566 days.

(21) Appl. No.: 14/418,801

(22) PCT Filed: Jul. 10, 2013

(86) PCT No.: PCT/KR2013/006109
§ 371 (c)(1),
(2) Date: Jan. 30, 2015

(87) PCT Pub. No.: WO2014/021561
PCT Pub. Date: Feb. 6, 2014

(65) Prior Publication Data
US 2015/0209467 A1    Jul. 30, 2015

(30) Foreign Application Priority Data
Aug. 3, 2012 (KR) .................. 10-2012-0085420

(51) Int. Cl.
| | |
|---|---|
| *A61K 36/718* | (2006.01) |
| *A61L 15/40* | (2006.01) |
| *A61F 13/84* | (2006.01) |
| *A61K 8/02* | (2006.01) |
| *A61Q 17/00* | (2006.01) |
| *A61K 8/97* | (2017.01) |
| *A61L 15/28* | (2006.01) |
| *A61L 15/44* | (2006.01) |
| *B65B 5/00* | (2006.01) |
| *B65B 55/02* | (2006.01) |

(52) U.S. Cl.
CPC .......... *A61L 15/40* (2013.01); *A61F 13/8405* (2013.01); *A61K 8/0208* (2013.01); *A61K 8/97* (2013.01); *A61L 15/28* (2013.01); *A61L 15/44* (2013.01); *A61Q 17/005* (2013.01); *B65B 5/00* (2013.01); *B65B 55/02* (2013.01); *A61F 2013/8414* (2013.01); *A61L 2300/404* (2013.01); *A61L 2300/41* (2013.01)

(58) Field of Classification Search
CPC .................................................... A61K 36/718
USPC ........................................................ 424/773
See application file for complete search history.

(56) References Cited

FOREIGN PATENT DOCUMENTS

| | | | |
|---|---|---|---|
| CN | 1097337 A | | 1/1995 |
| CN | 1124158 A | * | 6/1996 |
| CN | 1136447 A | | 11/1996 |
| CN | 1670165 A | | 9/2005 |
| CN | 101579273 B | | 1/2013 |
| JP | 11-200296 A | | 7/1999 |
| JP | 2005-287710 A | | 10/2005 |
| JP | 2005-306779 A | | 11/2005 |
| JP | 2008094736 A | * | 4/2008 |
| JP | 2010-202604 A | | 9/2010 |
| KR | 20040078859 A | * | 9/2004 |
| KR | 10-0553265 B1 | | 2/2006 |
| KR | 10-2009-0029022 A | | 3/2009 |
| KR | 10-1136464 B1 | | 4/2012 |
| KR | 10-2012-0063076 A | | 6/2012 |
| KR | 10-2005-0002715 A | | 10/2013 |

OTHER PUBLICATIONS

International Search Report, Korean Application No. PCT/KR2013/006109 dated Oct. 31, 2013.

* cited by examiner

*Primary Examiner* — Christopher R Tate
*Assistant Examiner* — Deborah A Davis
(74) *Attorney, Agent, or Firm* — The Dobrusin Law Firm, P.C.

(57) ABSTRACT

The present invention relates to a wet tissue containing a hot water extract of *Coptidis Rhizoma* extracted under high temperature and high pressure conditions, or a distillate thereof, and more specifically, to a wet tissue containing a hot water extract of *Coptidis Rhizoma* obtained by mixing 2,000-8,000 parts by weight of water on the basis of 100 parts by weight of *Coptidis Rhizoma* and extracting the same under high temperature and high pressure conditions of 120-131° C. and 1.2-2.8 atm, respectively, or a distillate thereof. The wet tissue containing a hot water extract of *Coptidis Rhizoma* or a distillate thereof shows remarkable antibacterial and fungicidal activities against pathogenic microorganisms existing in the skin and has an excellent inflammation inhibitory effect, and thus can be readily used for cleaning the skin and alleviating various inflammatory diseases.

6 Claims, 2 Drawing Sheets

[FIG. 1]

(Step 1) Extracting 100 parts by weight of Coptidis rhizoma with 2000-8000 parts by weight of water under the high temperature and high pressure conditions of 120-131 °C and 1.2-2.8 atm to prepare a hot-water extract of Coptidis rhizome

↓

(Step 2) Spraying 200-400 parts by weight of the hot-water extract of Coptidis rhizoma prepared in step (1) onto 100 parts by weight of a fabric for wet tissue to absorb the hot-water extract of Coptidis rhizoma into the fabric for wet tissue

↓

(Step 3) Hermetically packaging and sterilizing the fabric for wet tissue absorbed with the hot-water extract of Coptidis rhizome, thereby manufacturing a wet tissue containing the hot-water extract of Coptidis rhizome

[FIG. 2]

(Step 1) Extracting 100 parts by weight of Coptidis rhizoma with 2000-8000 parts by weight of water under the high temperature and high pressure conditions of 120-131°C and 1.2-2.8 atm to prepare a hot-water extract of Coptidis rhizome, distilling the hot-water extract of Coptidis rhizome to obtain vapor, and condensing the vapor, thereby preparing a distillate of hot-water extract of Coptidis rhizome,

↓

(Step 2) Spraying 200-400 parts by weight of the distillate of hot-water extract of Coptidis rhizoma prepared in step (1) onto 100 parts by weight of a fabric for wet tissue to absorb the distillate of hot-water extract of Coptidis rhizoma into the fabric for wet tissue

↓

(Step 3) Hermetically packaging and sterilizing the fabric for wet tissue absorbed with the distillate of hot-water extract of Coptidis rhizome, thereby manufacturing a wet tissue containing the distillate of hot-water extract of Coptidis rhizome

WET TISSUE CONTAINING HOT WATER EXTRACT OF COPTIDIS RHIZOMA EXTRACTED UNDER HIGH TEMPERATURE AND HIGH PRESSURE CONDITIONS

CROSS-REFERENCE TO RELATED APPLICATION

This application is a Section 371 National Stage Application of International Application No. PCT/KR2013/006109, filed Jul. 10, 2013, the contents of which is hereby incorporated by reference in its entirety.

TECHNICAL FIELD

The present invention relates to a wet tissue containing either a hot-water extract of *Coptidis rhizome* or a distillate of the extract. The hot-water extract of *Coptidis rhizome* is prepared by mixing 100 parts by weight of *Coptidis rhizoma* with 2000-8000 parts by weight of water and extracting under the high temperature and high pressure conditions of 120-131° C. and 1.2-2.8 atm.

BACKGROUND ART

Wet tissue is manufactured by adding water to a fabric for wet tissue, such as natural pulp, cotton, Ingeo, Tancel, natural fiber fabric, nonwoven fabric, synthetic fiber fabric, mixed fiber fabric, etc., and sterilizing the fabric, and is used for skin cleansing. It is produced in various forms, including wet tissue for oral cavity care, wet tissue for baby wipes, wet tissue for women, disposable towel, multipurpose wet tissue, etc. Because it is simple and convenient to use, the demand for wet tissue is increasing rapidly. Because this product is brought into direct contact with the human skin, it should be highly safe for the skin, should have an excellent ability to remove foreign matter and pathogenic microorganisms from the skin, and should also have the effect of improving skin conditions.

Meanwhile, currently commercially available wet tissue products mostly contain surfactants, chemical preservatives, fragrances, alcohols and the like, and particularly, these wet tissue products have been produced such that surfactants will function as a main component to dissolve and wipe away dirt. If such components come into contact with sensitive skin areas, they can cause skin irritation. Even if wet tissue products are not irritative, these merely act to wipe the skin, and there is a limit to removing bacteria from the skin using these wet tissue products. In addition, some time ago, the detection of methylparaben, a toxic chemical preservative, in wet tissue for oral cavity care, was reported, and thus the consumer's distrust of wet tissue products is increasing. For this reason, environmentally friendly wet tissue products containing no chemicals are receiving attention, but the safety of these products has not yet been proven.

As used herein, the term "*Coptidis rhizoma*" refers to the rhizome of *Coptis japonica* Makino or other plants of the same genus (*Rammculaceae*). The book "Illustrated Book of Korean Medicinal Herbs" describes that *Coptidis rhizoma* is used for various inflammations and is useful for the treatment of dermatitis. Also, the book "Dong-ui-chi-ryo" describes that *Coptidis rhizoma* can be used as a bitter stomachic, a sedative and an anti-inflammatory agent, and is used for congestion, inflammatory diseases, palpitation, mental anxiety, abdominal pain, diarrhea, dysentery, hemorrhage, etc. The book "Bon-cho-shin-pyeon" describes that *Coptidis rhizoma* has the effects of suppressing vomiting, eliminating thirst, treating a facial burn and preserving a tranquil mind. Also, it is known that *Coptidis rhizoma* is widely used for the treatment of stomatitis, glossitis, oral angulitis, a swell, various inflammations, particularly, ocular disease or otitis media, etc. Also, the book "Shin-Nong-Bon Cho-Kyung" describes that *Coptidis rhizoma* has the effects of alleviating eye pain caused by fever, alleviating tearing caused by eyelid injury, improving sight, and treating dysentery or abdominal pain.

*Phellodendron* bark is the bark of *Phellodendron amurense* Ruprecht or other plants of the same genus (*Rutaceae*). It is known that *Phellodendron* bark has antibacterial activity and acts to eliminate moisture and fever. The book "Bon-cho-gang-mok" describes that *Phellodendron* bark is used for the treatment of vaginal discharge, flooding and spotting, skin abscess in the pubic region, etc. In folk remedies, *Phellodendron* bark is used for eczema, lymphadenitis, chronic dermatophytosis, stomatitis, a burn, a cut, etc.

*Scutellaria* root is the root of *Scutellaria baicalensis* Georgi. It is known that *Scutellaria* root is used as an antipyretic, a diuretic, an antidiarrheal, an expectorant and an anti-inflammatory agent, and has excellent antibacterial activity. The book "Dong-ui-chi-ryo" describes that *Scutellaria* root is mainly used as an anti-inflammatory agent and a fever lowering agent, and is used for congestion, inflammation, disease with fever, abdominal pain, diarrhea, respiratory infection, coughing, jaundice caused by damp heat, inflammatory conjunctivitis, etc.

*Cassia obtusifolia* L. is also called (*Cassia tora* L. It is native to North America and is cultivated for medicinal use. It has a height of about 1 m. It has an even-pinnately compound leaf with 2-4 pairs of leaflets. The leaflet has an egg shape and is 3-4 cm in length. On June to August, yellow flowers bloom from the leaf axil. It is an annual plant belonging to the family Fabaceae, and is known to contain large amounts of kaempherol, anthraquinone and the like, which are precursors of vitamin C, emodin, carotin and vitamin A. Also, it is known to have a good therapeutic effect against stomatitis, and have the effect of inhibiting the growth of dermatophyte, and exhibit an antifungal effect. The seed of *Cassia obtusifolia* L. has the effects of promoting urination, alleviating constipation and improving sight, and thus is used for habitual constipation, hypertension, acute conjunctivitis, corneal opacity, etc., and is also roasted, boiled and drank like tea.

*Glycyrrhizae* radix is the radix of (*Glycyrrhiza uralensis* Fischer. *Glycyrrhiza glabra* L. or other plants of the same genus, which is used in Korea and Japan. In China, the dried radix of *Glycyrrhiza uralensis* Fischer, (*Glycyrrhiza glabra* L. or *Glycyrrhiza inflata* Batal is used. It grows in Russia (Siberia), Iran, Afghanistan, Pakistan, China (Gansu providence, and Xinjiang providence), mongo, etc., and is also cultivated in Korea. *Glycyrrhiza glabra* L. is distributed in Southern Europe, Central Asia, China, etc. *G. glabra* var. typical, *G. glabra* var. *glanduliferra*, etc., which are variants of *Glycyrrhiza glabra* L. are not used for medicinal purposes. The outer peel of *Glycyrrhizae* radix is red or dark brown in color, has vertical furrows, and sometimes has lenticels, eye buds and scale leaves attached thereto. Peeled *Glycyrrhizae* radix has a light yellow surface and is fibrous. It is also called "Kuk-No", "Mi-Cho", "Mil-Gam", "Mil-Cho", "Yeong-Tong", "Cheom-Cho", or "Ro-Cho". *Glycyrrhizae* radix is known to neutralize the poison of all drugs, alleviate the chill and fever of the viscera, promote blood circulation, and strengthen muscle and bone. It acts to neutralize poison, and is effective against hepatitis, urticaria, dermatitis, eczema, etc. In addition, it has antitussive, expectorant, muscular relaxation, urination and anti-inflammatory effects, and acts to suppress peptic ulcer.

*Hagocho* is the whole plant of perennial *Prunella vulgaris* var. *aleutica, Prunella vulgaris* var. *asiatica, Prunella vulgaris* var. *lilacina* for. *albiflora*, etc., which belong to the family Lamiaceae. It is known that *Hagocho* is cold in nature, is not poisonous, and has fever alleviating, poison-neutralizing and antibacterial effects. Also, it is known to have the effects of suppressing swells or inflammation, and particularly, have a great therapeutic effect against ocular diseases.

*Houttuyniae herba* refers to the flowering aerial part of *Houttuynia cordata* Thunberg belonging to the family Sauiuraceae in Korea. It is called "ten drugs" in Japan. In China, the whole plant or aerial part of *Houttuyniae herba* is used. *Houttuyniae herba* smells fishy. The leaf thereof smells fishy when it is rubbed, and is hot in taste and slightly cold in nature. *Houttuyniae herba* has excellent effects of alleviating a fever and draining a wound, and thus is used for coughing caused by lung abscess, bloody pus spitting, pneumonia, acute/chronic bronchitis, enteritis, urinary tract infection, swells, etc. Also, it acts to lower fever and promote urination. In addition, it was reported to have antimicrobial, immune boosting, anti-inflammatory, diuretic and antitussive effects.

Meanwhile, the present inventors have made extensive efforts to overcome various problems involved in commercially available wet tissue products, and as a result, have found that a wet tissue containing a hot-water extract of *Coptidis rhizome*, prepared by mixing 100 parts by weight of *Coptidis rhizoma* with 2000-8000 parts by weight of water and extracting under the high temperature and high pressure conditions of 120-131° C. and 1.2-2.8 atm, has excellent antibacterial and anti-inflammatory effects, thereby completing the present invention.

In prior art technologies relating to wet tissues containing a *Coptidis rhizome* extract, Korean Patent No. 553265 discloses a wet tissue containing electrolyzed water, a *Quercus serrata* extract and a *Coptidis rhizome* extract, and Korean Patent Laid-Open Publication No. 2005-0002715 discloses a wet tissue containing various herbal medicinal components, including *Coptidis rhizome*. Also, Korean Patent Laid-Open Publication No. 2012-0063076 discloses a wet tissue for preventing or treating vaginitis, which contains various herbal medicinal components, including *Coptidis rhizome*. However, it appears that the wet tissues according to the above prior art technologies definitely differs from the wet tissue of the present invention, which contains either a hot-water extract of *Coptidis rhizome*, or a distillate of the extract.

DISCLOSURE

Technical Problem

It is an object of the present invention to provide a wet tissue containing either a hot-water extract of *Coptidis rhizome* or a distillate of the extract. The hot-water extract of *Coptidis rhizome* is prepared by mixing 100 parts by weight of *Coptidis rhizoma* with 2000-8000 parts by weight of water and extracting under the high temperature and high pressure conditions of 120-131° C. and 1.2-2.8 atm.

Technical Solution

The present invention is directed to a wet tissue containing a hot-water extract of *Coptidis rhizome*, prepared by mixing 100 parts by weight of *Coptidis rhizoma* with 2000-8000 parts by weight of water and extracting under the high temperature and high pressure conditions of 120-131° C. and 1.2-2.8 atm.

The hot-water extract of *Coptidis rhizoma* may be prepared from 100 parts by weight of *Coptidis rhizoma* together with 1-50 parts by weight of one or more medicinal herbs selected from the group consisting of *Glycyrrhizae* radix, *Cassia obtusifolia* L., *Houttuyniae herba*, *Hagocho*, *Phellodendron* bark, and *Scutellaria* root.

The wet tissue containing the hot-water extract of *Coptidis rhizoma* may be manufactured by spraying 200-400 parts by weight of the hot-water extract of *Coptidis rhizoma* onto 100 parts by weight of a fabric for wet tissue to absorb the hot-water extract of *Coptidis rhizome* into the fabric for wet tissue, and sealing, hermetically packaging and sterilizing the fabric for wet tissue absorbed with the hot-water extract of *Coptidis rhizome*.

The fabric for wet tissue may be selected from the group consisting of natural pulp, cotton, Ingeo, Tancel, natural fiber fabric, mixed fiber fabric, nonwoven fabric, and synthetic fiber fabric.

The fabric for wet tissue may be hermetically packaged, and then sterilized using a conventional sterilization method. Preferably, the fabric for wet tissue may be sterilized either under the high temperature and high pressure conditions of 120-131° C. and 1.2-2.8 atm or by irradiation with gamma rays for 15-30 hours.

In another aspect, the present invention provides a cotton swab, a gauze, a mask, a diaper, a sanitary napkin or the like, which contains the hot-water extract of *Coptidis rhizome*.

The present invention also provides a method for manufacturing a wet tissue containing a hot-water extract of *Coptidis rhizome*, the method comprising the steps of:

(1) mixing 100 parts by weight of *Coptidis rhizoma* with 2000-8000 parts by weight of water and extracting under the high temperature and high pressure conditions of 120-131° C. and 1.2-2.8 atm to prepare the hot-water extract of *Coptidis rhizome*;

(2) spraying 200-400 parts by weight of the hot-water extract of *Coptidis rhizoma* prepared in step (1) onto 100 parts by weight of a fabric for wet tissue to absorb the hot-water extract of *Coptidis rhizoma* into the fabric for wet tissue; and (3) hermetically packaging and sterilizing the fabric for wet tissue absorbed with the hot-water extract of *Coptidis rhizome*.

Sterilization of the fabric for wet tissue after hermetically packaging in step (3) may be performed by sterilizing the fabric for wet tissue under the high temperature and high pressure conditions of 120-131° C. and 1.2-2.8 atm or irradiating the fabric for wet tissue with gamma rays for 15-30 hours.

The present invention also provides a method for manufacturing an article selected from the group consisting of a cotton swab, gauze, a mask, a diaper and a sanitary napkin, the method comprising the steps of:

(A) mixing 100 parts by weight of *Coptidis rhizoma* with 2000-8000 parts by weight of water and extracting under the high temperature and high pressure conditions of 120-131° C. and 1.2-2.8 atm to prepare a hot-water extract of *Coptidis rhizoma*;

(B) spraying 200-400 parts by weight of the hot-water extract of *Coptidis rhizome* prepared in step (A) onto 100 parts by weight of one material selected from the group consisting of cotton, fabric for gauze, cotton fabric, natural fiber fabric, synthetic fiber fabric, mixed fiber fabric and nonwoven fabric to absorb the hot-water extract of *Coptidis rhizome* into the selected material;

(C) drying and sterilizing the material absorbed with the hot-water extract of *Coptidis rhizome*; and (D) manufacturing an article selected from the group consisting of a cotton swab, gauze, a mask, a diaper and a sanitary napkin using the dried and sterilized material of step (C), and packaging and sterilizing the manufactured article.

The present invention also provides an article selected from the group consisting of a wet tissue, a cotton swab, gauze, a mask, a diaper and a sanitary napkin, the article containing a distillate obtained by mixing 100 parts by weight of *Coptidis rhizoma* with 2000-8000 parts by weight of water and extracting under the high temperature and high pressure conditions of 120-131° C. and 1.2-2.8 atm to prepare a hot-water extract of *Coptidis rhizome*, distilling the hot-water extract of *Coptidis rhizome* to obtain vapor, and condensing the obtained vapor.

The wet tissue containing a distillate of hot-water extract of *Coptidis rhizome* may be manufactured by a method comprising the steps of:

(1) mixing 100 parts by weight of *Coptidis rhizoma* with 2000-8000 parts by weight of water and extracting under the high temperature and high pressure conditions of 120-131° C. and 1.2-2.8 atm to prepare a hot-water extract of *Coptidis rhizome*, distilling the hot-water extract of *Coptidis rhizome* to obtain vapor, and condensing the obtained vapor, thereby preparing a distillate of hot-water extract of *Coptidis rhizome*;

(2) spraying 200-400 parts by weight of the distillate of hot-water extract of *Coptidis rhizoma* prepared in step (1) onto 100 parts by weight of a fabric for wet tissue to absorb the distillate of hot-water extract of *Coptidis rhizoma* into the fabric for wet tissue; and (3) hermetically packaging and sterilizing the fabric for wet tissue absorbed with the distillate of hot-water extract of *Coptidis rhizoma*.

In addition, the article selected from the group consisting of a cotton swab, gauze, a mask, a diaper and a sanitary napkin, which contains the distillate of hot-water extract of *Coptidis rhizome*, may be manufactured by a method comprising the steps of:

(A) mixing 100 parts by weight of *Coptidis rhizoma* with 2000-8000 parts by weight of water and extracting under the high temperature and high pressure conditions of 120-131° C. and 1.2-2.8 atm to prepare a hot-water extract of *Coptidis rhizome*, distilling the hot-water extract of *Coptidis rhizome* to obtain vapor, and condensing the obtained vapor, thereby preparing a distillate of hot-water extract of *Coptidis rhizome*;

(B) spraying 200-400 parts by weight of the distillate of hot-water extract of *Coptidis rhizome* prepared in step (A) onto 100 parts by weight of one material selected from the group consisting of cotton, fabric for gauze, cotton fabric, natural fiber fabric, synthetic fiber fabric, mixed fiber fabric and nonwoven fabric to absorb the distillate of hot-water extract of *Coptidis rhizome* into the selected material;

(C) drying and sterilizing the material absorbed with the distillate of hot-water extract of *Coptidis rhizome*; and (D) manufacturing an article selected from the group consisting of a cotton swab, gauze, a mask, a diaper and a sanitary napkin using the dried and sterilized material of step (C), and packaging and sterilizing the manufactured article.

Hereinafter, the present invention will be described in detail.

The present invention is directed to a wet tissue containing either a hot-water extract of *Coptidis rhizome* or a distillate of the extract. The hot-water extract of *Coptidis rhizome* is prepared by mixing 100 parts by weight of *Coptidis rhizoma* with 2000-8000 parts by weight of water and extracting under the high temperature and high pressure conditions of 120-131° C. and 1.2-2.8 atm. The wet tissue according to the present invention has antibacterial, anti-inflammatory, cleaning and washing effects.

If less than 2000 parts by weight or more than 8000 parts by weight of water is added to 100 parts by weight of *Coptidis rhizome*, the efficiency of extraction will be low.

The hot-water extract of *Coptidis rhizome* may be used after it is filtered to remove solids or filtered and concentrated. However, it is preferably used after filtration without concentration, because the concentration process incurs costs.

If the extraction of (*Coptidis rhizome* is performed at a temperature higher than 120-131 and a pressure higher than 1.2-2.8 atm, the active ingredient of *Coptidis rhizome* will not be easily extracted, and thus the cleaning, washing, antibacterial and anti-inflammatory effects of the extract will be reduced. Also, if the extraction of *Coptidis rhizome* is performed at a temperature lower than 120-131° C. and a pressure lower than 1.2-2.8 atm, the active ingredient of *Coptidis rhizome* will be broken, and thus the antibacterial, anti-inflammatory, wound healing, cleaning and washing effects of the extract will be reduced. In addition, if the extraction of *Coptidis rhizome* is performed at a temperature lower than 120-131° C. and a pressure lower than 1.2-2.8 atm, the cost of the extraction will be increased. However, if the extraction of *Coptidis rhizome* is performed at a ultrahigh pressure (less than 1100 atm) exceeding 2.8 atm, the breakdown of the active ingredient can be reduced when the extraction temperature is maintained at 100° or less, and thus the extract can be used as a hot-water extract for a wet tissue according to the present invention.

Also, the extraction time of *Coptidis rhizome* is not limited, but is preferably 10 minutes to 24 hours, more preferably 10 minutes to 9 hours, even more preferably 10-60 minutes, and most preferably 20-40 minutes. If the extraction time is less than 10 minutes, the active ingredient of *Coptidis rhizome* will not be easily extracted, and thus the antibacterial, anti-inflammatory, cleaning and washing effects of the extract will be reduced. If the extraction time is more than 24 hours, the amount of active ingredient extracted will no longer be increased, and the production cost will be increased.

Also, when *Coptidis rhizoma* is extracted together with one or more medicinal herbs selected from the group consisting of *Glycyrrhizae* radix, *Cassia obtusifolia* L., *Houttuyniae herba*, *Hagocho*, *Phellodendron* bark, and *Scutellaria* root, the antibacterial, anti-inflammatory, cleaning and washing effects of the extract can be increased.

The distillate of hot-water extract of *Coptidis rhizome* can be prepared by mixing 100 parts by weight of *Coptidis rhizoma* with 2000-8000 parts by weight of water, extracting under the high temperature and high pressure conditions of 120-131° C. and 1.2-2.8 atm to prepare a hot-water extract of *Coptidis rhizome*, distilling the hot-water extract of *Coptidis rhizome* to obtain vapor, and condensing the obtained vapor. The temperature of distillation in the preparation of the distillate of hot-water extract of *Coptidis rhizome* may be the boiling temperature of water, but is preferably 100-131° C., and most preferably 120-131° C. As the distillation temperature increases, the distillation time decreases, and thus the process time decreases.

Also, to prepare the distillate of hot-water extract of *Coptidis rhizome*, 100 parts by weight of *Coptidis rhizome* may be extracted together with 1-50 parts by weight of one or more medicinal herbs selected from the group consisting of *Glycyrrhizae* radix, *Cassia obtusifolia* L., *Houttuyniae herba*, *Hagocho*, *Phellodendron* bark, and *Scutellaria* root.

The distillate contains volatile substances contained in the hot-water extract of *Coptidis rhizome*, and has higher antibacterial, anti-inflammatory, cleaning and washing effects compared to the hot-water extract of *Coptidis rhizome*.

The distillate may be used after concentration, but is preferably used after condensation of the vapor. This is because the concentration process can incurs costs, and the antibacterial, anti-inflammatory, cleaning and washing effects as described above are sufficiently maintained even when the distillate is not concentrated.

The wet tissue of the present invention can be manufactured by a conventional process of spraying or impregnating the hot-water extract of *Coptidis rhizome* or a distillate thereof into a fabric for wet tissue. Preferably, the spraying process is used.

The fabric for wet tissue may be used as a single sheet, but it may also be manufactured by putting 2-3 sheets one upon another and forming a plurality of waves thereon by a thermal compression method or the like. For example, 2 sheets of fabric for wet tissue are put one upon another, and then thermally treated to form a lattice shape, a protrusion/depression shape or an embossed shape.

The wet tissue of the present invention may contain, in addition to the hot-water extract of *Coptidis rhizome* or a distillate thereof, conventional additives. Such additives include surfactants, humectants, preservatives, fragrances, sterilizing agents, deodorants, etc. The surfactants include dodecyl benzene sulfonate and lauryl trimethyl ammonium, and the humectants include chamomile oil, and the preservatives include phenoxyethanol, methylparaben, and ethylparaben. The fragrances include phenoxyethanol, herbs, green tea extracts, chamomile flower extracts, and limonene, the sterilizing agents include ethylalcohol, and the deodorants include chitosan, but are not limited thereto, and components that are generally added to wet tissue products may be used. Most preferably, the wet tissue of the present invention contains only the hot-water extract of *Coptidis rhizome* or a distillate thereof. Meanwhile, these additive components may be added to an amount of 0.01-5 parts by weight based on 100 parts by weight of the hot-water extract of *Coptidis rhizome* or a distillate thereof.

Meanwhile, the extraction under high-temperature and high-pressure conditions in the present invention may be performed using a high-temperature and high-pressure extractor that is generally used for the extraction of herbal materials. Also, spraying of the hot-water extract of *Coptidis rhizome* onto a fabric for wet tissue may be performed using a steam injector, a sprayer or the like, which is generally used for food material processing or steam injection.

In addition, according to the present invention, a wet tissue for oral cavity care containing the hot-water extract of *Coptidis rhizome* or a distillate thereof can be manufactured. Preferably, the wet tissue may contain the hot-water extract of *Coptidis rhizome* prepared by extracting *Coptidis rhizome* together with *Glycyrrhizae* radix, or a distillate thereof. Also, when the wet tissue is to be used for oral cavity care, it may further contain sweeteners such as xylitol, saccharin, stevioside or the like.

In still another aspect, the present invention provides articles such as a cotton swab, a gauze, a mask, a diaper, a sanitary napkin or the like, which contains the hot-water extract of *Coptidis rhizome* or a distillate thereof. This article, such as a cotton swab, gauze, a mask, a diaper, a sanitary napkin or the like, can be manufactured by spraying the hot-water extract of *Coptidis rhizome* or a distillate thereof onto one material selected from among cotton, fabric for gauze, cotton fabric and nonwoven fabric, drying the sprayed article, and sterilizing and packaging the dried article. Herein, for the diaper or the sanitary napkin, an outer cover that comes into direct contact with the skin can be manufactured using one selected from among cotton, fabric for gauze, cotton fabric and nonwoven fabric. In addition, these articles are preferably sterilized by irradiation with gamma rays.

Meanwhile, a cotton swab containing the hot-water extract of *Coptidis rhizome* or a distillate thereof may be manufactured after separately treating cotton with the hot-water extract of *Coptidis rhizome*, or by treating a manufactured cotton swab with the hot-water extract of *Coptidis rhizome* or a distillate thereof.

Advantageous Effects

The present invention relates to a wet tissue containing either a hot-water extract of *Coptidis rhizome* prepared by extraction under high-temperature and high-pressure conditions or a distillate of the extract, and more preferably, to a wet tissue containing either a hot-water extract of *Coptidis rhizome* or a distillate of the extract, which is prepared by mixing 100 parts by weight of *Coptidis rhizoma* with 2000-8000 parts by weight of water and extracting under the high temperature and high pressure conditions of 120-131° C. and 1.2-2.8 atm. The wet tissue containing the hot-water extract of *Coptidis rhizome* or a distillate thereof has excellent antibacterial and antifungal activities against pathogenic microorganisms present on the skin, shows excellent anti-inflammatory effects, and thus can be effectively used for skin cleaning and the alleviation of various inflammatory diseases.

BRIEF DESCRIPTION OF THE DRAWINGS

The above objects, other features and advantages of the present invention will become more apparent by describing the preferred embodiments thereof with reference to the accompanying drawings, in which:

FIG. 1 is a flow chart showing a process for manufacturing a wet tissue containing a hot-water extract of *Coptidis rhizome* according to the present invention; and FIG. 2 is a flow chart showing a process for manufacturing a wet tissue containing a distillate of hot-water extract of *Coptidis rhizome* according to the present invention.

PREFERRED EMBODIMENTS OF THE INVENTION

Hereinafter, preferred examples of the present invention will be described in detail. The present invention may, however, be embodied in many different forms and should not be construed as being limited to the examples set forth herein. Rather, these examples are provided so that this disclosure will be thorough and complete and will fully convey the concept of the invention to those skilled in the art.

Example 1: Preparation of Hot-Water Extract of *Coptidis rhizome* and Distillate Thereof Examples 1-1 to 1-24: Hot-Water Extract of *Coptidis rhizome*

According to the compositions shown in Table 1 below, *Coptidis rhizome* was mixed with water, and then extracted under the high temperature and high pressure conditions of 120-131° C. and 1.2-2.8 atm, thereby preparing hot-water extracts of *Coptidis rhizome* (a liquid phase remaining after removal of herbal solids after extraction was used, and herbal solids in the extracts in the Examples and the Comparative Examples were removed in the same manner). In addition, to enhance the antibacterial and antimicrobial effects of the hot-water extract of *Coptidis rhizome*, an extract of a mixture of *Coptidis rhizome* with at least one of *Glycyrrhizae* radix, *Cassia obtusifolia* L., *Houttuyniae herba*, *Hagocho*, *Phellodendron* bark, and *Scutellaria* root was prepared. Herein, the hot-water extract of *Coptidis rhizome* was prepared using a high-temperature and high-pressure extractor (Daerin Machinery Co., Ltd., Korea). Also, the volume of each of the extracts was adjusted to have the same volume as that of Example 1-1 by concentration or the addition of water.

Example 1-28

Vapor obtained by distilling the extract of Example 1-13 at a temperature of 120-131° C. was condensed, thereby obtaining a distillate of hot-water extract of *Coptidis rhizome*.

Example 2: Manufacture of Wet Tissues Containing Hot-Water Extract of *Coptidis rhizome* Prepared Under High Temperature and High Pressure Conditions or Distillate Thereof 340 g of the extract or distillate of Example 1 was sprayed and absorbed onto 63 cotton tissue fabric sheets (16 cm×18 cm; 100 g) (see Table 2). Next, the tissue treated with the extract or distillate was sealed and packaged, and then sterilized using a Hi-RETORT STERILIZER (Daerin

TABLE 1

| Conditions | Weight (g) | | | | | | | | Temperature (° C.) | Pressure (atm) | Time (min) |
| | *Coptidis rhizoma* | *Glycyrrhizae radix* | *Cassia obtusifolia* L. | *Houttuyniae herba* | *Hagocho* | *Scutellaria root* | *Phellodendron bark* | water | | | |
|---|---|---|---|---|---|---|---|---|---|---|---|
| Ex. 1-1  | 100 | — | — | — | — | — | — | 5000 | 120 | 2.0 | 30 |
| Ex. 1-2  | 100 | — | — | — | — | — | — | 2000 | 120 | 2.0 | 30 |
| Ex. 1-3  | 100 | — | — | — | — | — | — | 8000 | 120 | 2.0 | 30 |
| Ex. 1-4  | 100 | — | — | — | — | — | — | 5000 | 121 | 1.2 | 30 |
| Ex. 1-5  | 100 | — | — | — | — | — | — | 5000 | 120 | 2.0 | 20 |
| Ex. 1-6  | 100 | — | — | — | — | — | — | 5000 | 120 | 2.0 | 120 |
| Ex. 1-7  | 90  | 10 | — | — | — | — | — | 5000 | 120 | 2.0 | 30 |
| Ex. 1-8  | 90  | — | 10 | — | — | — | — | 5000 | 120 | 2.0 | 30 |
| Ex. 1-9  | 90  | — | — | 10 | — | — | — | 5000 | 120 | 2.0 | 30 |
| Ex. 1-10 | 80  | 20 | — | — | — | — | — | 5000 | 120 | 2.0 | 30 |
| Ex. 1-11 | 80  | — | 20 | — | — | — | — | 5000 | 120 | 2.0 | 30 |
| Ex. 1-12 | 80  | — | — | 20 | — | — | — | 5000 | 120 | 2.0 | 30 |
| Ex. 1-13 | 80  | — | — | — | 20 | — | — | 5000 | 120 | 2.0 | 30 |
| Ex. 1-14 | 80  | — | 10 | 10 | — | — | — | 5000 | 120 | 2.0 | 30 |
| Ex. 1-15 | 80  | — | — | 10 | 10 | — | — | 5000 | 120 | 2.0 | 30 |
| Ex. 1-16 | 80  | — | 10 | — | 10 | — | — | 5000 | 120 | 2.0 | 30 |
| Ex. 1-17 | 70  | — | 10 | 10 | 10 | — | — | 5000 | 120 | 2.0 | 30 |
| Ex. 1-18 | 70  | — | 30 | — | — | — | — | 5000 | 120 | 2.0 | 30 |
| Ex. 1-19 | 70  | — | — | 30 | — | — | — | 5000 | 120 | 2.0 | 30 |
| Ex. 1-20 | 70  | — | — | — | 30 | — | — | 5000 | 120 | 2.0 | 30 |
| Ex. 1-21 | 80  | — | — | — | — | 20 | — | 5000 | 120 | 2.0 | 30 |
| Ex. 1-22 | 80  | — | — | — | — | — | 20 | 5000 | 120 | 2.0 | 30 |
| Ex. 1-23 | 80  | — | — | — | — | 10 | 10 | 5000 | 120 | 2.0 | 30 |
| Ex. 1-24 | 100 | — | — | — | — | — | — | 5000 | 130 | 2.5 | 30 |

Examples 1-25 to 1-28: Distillate of Hot-Water Extract of *Coptidis rhizome*

Example 1-25

Vapor obtained by distilling the extract of Example 1-1 at a temperature of 120-131° C. was condensed, thereby obtaining a distillate of hot-water extract of *Coptidis rhizome*.

Example 1-26

Vapor obtained by distilling the extract of Example 1-8 at a temperature of 120-131° C. was condensed, thereby obtaining a distillate of hot-water extract of *Coptidis rhizome*.

Example 1-27

Vapor obtained by distilling the extract of Example 1-9 at a temperature of 120-131° C. was condensed, thereby obtaining a distillate of hot-water extract of *Coptidis rhizome*.

Machinery Co., Ltd., Korea), thereby obtaining wet tissues (sterilized at 1.2 atm and 121° C. for 15 minutes).

Meanwhile, wet tissues for oral cavity of Examples 2-7 and 2-10 were manufactured using an extract of a mixture of (*Coptidis rhizome* and *Glycyrrhizae* radix.

TABLE 2

| Wet tissue | Extract used |
|---|---|
| Example 2-1 | Extract of Example 1-1 |
| Example 2-2 | Extract of Example 1-2 |
| Example 2-3 | Extract of Example 1-3 |
| Example 2-4 | Extract of Example 1-4 |
| Example 2-5 | Extract of Example 1-5 |
| Example 2-6 | Extract of Example 1-6 |
| Example 2-7 | Extract of Example 1-7 |
| Example 2-8 | Extract of Example 1-8 |
| Example 2-9 | Extract of Example 1-9 |
| Example 2-10 | Extract of Example 1-10 |
| Example 2-11 | Extract of Example 1-11 |
| Example 2-12 | Extract of Example 1-12 |
| Example 2-13 | Extract of Example 1-13 |
| Example 2-14 | Extract of Example 1-14 |

TABLE 2-continued

| Wet tissue | Extract used |
|---|---|
| Example 2-15 | Extract of Example 1-15 |
| Example 2-16 | Extract of Example 1-16 |
| Example 2-17 | Extract of Example 1-17 |
| Example 2-18 | Extract of Example 1-18 |
| Example 2-19 | Extract of Example 1-19 |
| Example 2-20 | Extract of Example 1-20 |
| Example 2-21 | Extract of Example 1-21 |
| Example 2-22 | Extract of Example 1-22 |
| Example 2-23 | Extract of Example 1-23 |
| Example 2-24 | Extract of Example 1-24 |
| Example 2-25 | Extract of Example 1-25 |
| Example 2-26 | Extract of Example 1-26 |
| Example 2-27 | Extract of Example 1-27 |
| Example 2-28 | Extract of Example 1-28 |

Example 3: Manufacture of Cotton Swab and Gauze Containing Hot-Water Extract of *Coptidis rhizome*

240 g of the hot-water extract of *Coptidis rhizome* of Example 1-1 was sprayed onto 100 g of each of cotton and cotton gauze fabric and dried. Then, a cotton swab was manufactured using the cotton, and the cotton gauze fabric was cut to a suitable size to thereby manufacture wound dressing gauze. Next, the cotton swab and the gauze were hermetically packaged, and then sterilized by irradiation with gamma-rays for 20 hours, thereby manufacturing final articles.

Example 4: Manufacture of Cotton Swab and Gauze Containing Distillate of Hot-Water Extract of *Coptidis rhizome*

240 g of the distillate of hot-water extract of *Coptidis rhizome* of Example 1-25 was sprayed onto 100 g of each of cotton and cotton gauze fabric and dried. Then, a cotton swab was manufactured using the cotton, and the cotton gauze fabric was cut to a suitable size to thereby manufacture wound dressing gauze. Next, the cotton swab and the gauze were hermetically packaged, and then sterilized by irradiation with gamma-rays for 20 hours, thereby manufacturing final articles.

Comparative Example 1: Preparation of Hot-Water Extracts of *Coptidis rhizome* for Comparison According to the compositions shown in Table 3 below, *Coptidis rhizome* was mixed and extracted, thereby preparing hot-water extracts of *Coptidis rhizome* for comparison. Also, to compare the effects of the extracts, the weight of each extract was adjusted to the same weight as that of each of the extracts of Example 1 by addition of water or concentration.

TABLE 3

| | Weight (g) | | | | | | | | Temperature (° C.) | Pressure (atm) | Time (min) |
|---|---|---|---|---|---|---|---|---|---|---|---|
| Conditions | *Coptidis rhizoma* | *Glycyrrhizae radix* | *Cassia obtusifolia* L. | *Houttuyniae herba* | *Hagocho* | *Scutellaria* root | *Phellodendron* bark | water | | | |
| Comp. Ex. 1-1 | 100 | — | — | — | — | — | — | 5000 | 100 | 1.0 | 30 |
| Comp. Ex. 1-2 | 100 | — | — | — | — | — | — | 5000 | 90 | 1.0 | 30 |
| Comp. Ex. 1-3 | 100 | — | — | — | — | — | — | 5000 | 80 | 1.0 | 30 |
| Comp. Ex. 1-4 | 90 | 10 | — | — | — | — | — | 5000 | 100 | 1.0 | 30 |
| Comp. Ex. 1-5 | 90 | — | 10 | — | — | — | — | 5000 | 100 | 1.0 | 30 |
| Comp. Ex. 1-6 | 90 | — | — | 10 | — | — | — | 5000 | 100 | 1.0 | 30 |
| Comp. Ex. 1-7 | 80 | 20 | — | — | — | — | — | 5000 | 100 | 1.0 | 30 |
| Comp. Ex. 1-8 | 80 | — | 20 | — | — | — | — | 5000 | 100 | 1.0 | 30 |
| Comp. Ex. 1-9 | 80 | — | — | 20 | — | — | — | 5000 | 100 | 1.0 | 30 |
| Comp. Ex. 1-10 | 80 | — | — | — | 20 | — | — | 5000 | 100 | 1.0 | 30 |
| Comp. Ex. 1-11 | 80 | — | 10 | 10 | — | — | — | 5000 | 100 | 1.0 | 30 |
| Comp. Ex. 1-12 | 80 | — | — | 10 | 10 | — | — | 5000 | 100 | 1.0 | 30 |
| Comp. Ex. 1-13 | 80 | — | 10 | — | 10 | — | — | 5000 | 100 | 1.0 | 30 |
| Comp. Ex. 1-14 | 70 | — | 10 | 10 | 10 | — | — | 5000 | 100 | 1.0 | 30 |
| Comp. Ex. 1-15 | 70 | — | 30 | — | — | — | — | 5000 | 100 | 1.0 | 30 |
| Comp. Ex. 1-16 | 70 | — | — | 30 | — | — | — | 5000 | 100 | 1.0 | 30 |
| Comp. Ex. 1-17 | 70 | — | — | — | 30 | — | — | 5000 | 100 | 1.0 | 30 |
| Comp. Ex. 1-18 | 80 | — | — | — | — | 20 | — | 5000 | 100 | 1.0 | 30 |
| Comp. Ex. 1-19 | 80 | — | — | — | — | — | 20 | 5000 | 100 | 1.0 | 30 |
| Comp. Ex. 1-20 | 80 | — | — | — | — | 10 | 10 | 5000 | 100 | 1.0 | 30 |

TABLE 3-continued

| Conditions | Coptidis rhizoma | Glycyrrhizae radix | Cassia obtusifolia L. | Houttuyniae herba | Hagocho | Scutellaria root | Phellodendron bark | water | Temperature (° C.) | Pressure (atm) | Time (min) |
|---|---|---|---|---|---|---|---|---|---|---|---|
| Comp. Ex. 1-21 | — | 100 | — | — | — | — | — | 5000 | 120 | 2.0 | 30 |
| Comp. Ex. 1-22 | — | — | 100 | — | — | — | — | 5000 | 120 | 2.0 | 30 |
| Comp. Ex. 1-23 | — | — | — | 100 | — | — | — | 5000 | 120 | 2.0 | 30 |
| Comp. Ex. 1-24 | — | — | — | — | 100 | — | — | 5000 | 120 | 2.0 | 30 |
| Comp. Ex. 1-25 | — | — | — | — | — | 100 | — | 5000 | 120 | 2.0 | 30 |
| Comp. Ex. 1-26 | — | — | — | — | — | — | 100 | 5000 | 120 | 2.0 | 30 |
| Comp. Ex. 1-27 | 100 | — | — | — | — | — | — | 5000 | 95 | 1.5 | 30 |

Comparative Example 2: Manufacture of Wet Tissue Containing Organic Solvent Extract of *Coptidis rhizome*

According to the compositions shown in Table 4 below, *Coptidis rhizome* extracts were prepared using 70% ethanol aqueous solution in place of water. Each of the extracts was filtered to remove herbal solids, and the filtrate was concentrated under reduced pressure to remove ethanol. Then, the weight of each extract was adjusted to the same weight as that of each of the extracts of Example 1 by addition of water.

Meanwhile, extracts of Comparative Examples 2-8 and 2-9 were prepared in the following manner. *Coptidis rhizome* and 1,3-butyleneglycol or 70% ethanol solvent were placed in an extractor, which was then completely sealed so that pressure did not leak. The extraction of *Coptidis rhizome* was performed while the internal temperature of the extractor was elevated stepwise to 85° C. or 95° C. over 1 hour and maintained at that temperature for 3 hours. The extraction pressure was maintained at 1.2 atm or 1.5 atm. Also, to increase the efficiency of extraction, a stirrer having an anchor and a paddle was used, and the stirring speed during the extraction was maintained at 40-50 rpm. After completion of the extraction, the reactor was cooled to room temperature over 1 hour, and then the extract was filtered through a Nutsch filter to remove *Coptidis rhizome* solids. The filtrate was further filtered through filter paper (pore size: 1 μm or less), and distilled under reduced pressure to remove the organic solvent. The volume of the distillate was adjusted to the same volume of each extract of Example 1 by adding water thereto.

TABLE 4

| Conditions | Coptidis rhizoma | Glycyrrhizae radix | Cassia obtusifolia L. | Houttuyniae herba | Hagocho | Scutellaria root | Phellodendron bark | 70% ethanol | 1,3 butyleneglycol | Temperature (° C.) | Pressure (atm) | Time (min) |
|---|---|---|---|---|---|---|---|---|---|---|---|---|
| Comp. Ex. 2-1 | 100 | — | — | — | — | — | — | 500 | — | 80 | 1.0 | 30 |
| Comp. Ex. 2-2 | 80 | 20 | — | — | — | — | — | 500 | — | 80 | 1.0 | 30 |
| Comp. Ex. 2-3 | 80 | — | 20 | — | — | — | — | 500 | — | 80 | 1.0 | 30 |
| Comp. Ex. 2-4 | 80 | — | — | 20 | — | — | — | 500 | — | 80 | 1.0 | 30 |
| Comp. Ex. 2-5 | 80 | — | — | — | 20 | — | — | 500 | — | 80 | 1.0 | 30 |
| Comp. Ex. 2-6 | 80 | — | — | — | — | 20 | — | 500 | — | 80 | 1.0 | 30 |
| Comp. Ex. 2-7 | 80 | — | — | — | — | — | 20 | 500 | — | 80 | 1.0 | 30 |
| Comp. Ex. 2-8 | 100 | — | — | — | — | — | — | — | 500 | 85 | 1.2 | 240 |
| Comp. Ex. 2-9 | 100 | — | — | — | — | — | — | 500 | — | 80 | 1.5 | 240 |

Comparative Example 3: Manufacture of Wet Tissues for Comparison

Wet tissues were manufactured in the same manner as described in Example 2, except that the extract shown in Table 5 below was sprayed onto a fabric for wet tissue.

TABLE 5

| Wet tissue | Extract used |
|---|---|
| Comparative Example 3-1 | Extract of Comparative Example 1-1 |
| Comparative Example 3-2 | Extract of Comparative Example 1-2 |
| Comparative Example 3-3 | Extract of Comparative Example 1-3 |

TABLE 5-continued

| Wet tissue | Extract used |
|---|---|
| Comparative Example 3-4 | Extract of Comparative Example 1-4 |
| Comparative Example 3-5 | Extract of Comparative Example 1-5 |
| Comparative Example 3-6 | Extract of Comparative Example 1-6 |
| Comparative Example 3-7 | Extract of Comparative Example 1-7 |
| Comparative Example 3-8 | Extract of Comparative Example 1-8 |
| Comparative Example 3-9 | Extract of Comparative Example 1-9 |
| Comparative Example 3-10 | Extract of Comparative Example 1-10 |
| Comparative Example 3-11 | Extract of Comparative Example 1-11 |
| Comparative Example 3-12 | Extract of Comparative Example 1-12 |
| Comparative Example 3-13 | Extract of Comparative Example 1-13 |
| Comparative Example 3-14 | Extract of Comparative Example 1-14 |
| Comparative Example 3-15 | Extract of Comparative Example 1-15 |
| Comparative Example 3-16 | Extract of Comparative Example 1-16 |
| Comparative Example 3-17 | Extract of Comparative Example 1-17 |
| Comparative Example 3-18 | Extract of Comparative Example 1-18 |
| Comparative Example 3-19 | Extract of Comparative Example 1-19 |
| Comparative Example 3-20 | Extract of Comparative Example 1-20 |
| Comparative Example 3-21 | Extract of Comparative Example 1-21 |
| Comparative Example 3-22 | Extract of Comparative Example 1-22 |
| Comparative Example 3-23 | Extract of Comparative Example 1-23 |
| Comparative Example 3-24 | Extract of Comparative Example 1-24 |
| Comparative Example 3-25 | Extract of Comparative Example 1-25 |
| Comparative Example 3-26 | Extract of Comparative Example 1-26 |
| Comparative Example 3-27 | Extract of Comparative Example 1-27 |
| Comparative Example 3-28 | Extract of Comparative Example 2-1 |
| Comparative Example 3-29 | Extract of Comparative Example 2-2 |
| Comparative Example 3-30 | Extract of Comparative Example 2-3 |
| Comparative Example 3-31 | Extract of Comparative Example 2-4 |
| Comparative Example 3-32 | Extract of Comparative Example 2-5 |
| Comparative Example 3-33 | Extract of Comparative Example 2-6 |
| Comparative Example 3-34 | Extract of Comparative Example 2-7 |
| Comparative Example 3-35 | Extract of Comparative Example 2-8 |
| Comparative Example 3-36 | Extract of Comparative Example 2-9 |
| Comparative Example 3-37 | Only water added |

Comparative Example 4: Manufacture for Cotton Swab and Gauze Containing Hot-Water Extract of *Coptidis rhizoma* for Comparison A cotton swab and gauze containing the hot-water extract of *Coptidis rhizome* were manufactured in the same manner as described in Example 3, except that the hot-water extract of *Coptidis rhizoma* of Comparative Example 1-1 was sprayed.

Experimental Example 1: Examination of Long-Term Storage Stability

The wet tissues of Example 2 and Comparative Example 3 were allowed to stand at room temperature (25 t) in a sealed and packaged state. At one month, the cover of the wet tissue package was opened, and 2 sheets of the tissue were taken out of the package and used in the experiment. Then, the cover of the wet tissue package was closed and the package was allowed to stand in the same manner as described above. At 3 months, two sheets of the tissue were taken out of the package and used in the experiment. At 6 months, two sheets of the tissue were finally taken out of the package and used in the experiment. Herein, the cover was carefully opened and closed so that the wet tissue would not be dried due to external conditions, and the package was stored in a closed space having a humidity of 80% or more.

Using the wet tissues taken at each point of time, the degree of growth of general bacterial in the wet tissue during each storage period was examined. Each of the taken wet tissues was stirred in a stomacher bag containing peptone water for 120 seconds, and then serially diluted. 0.1 ml of each of the dilutions was plated on a plate count agar (PCA) plate medium. Measurement of general bacteria was performed using 3M Petrifilm after the dilution was incubated on the PCA medium at 35° C. for 24 hours. The results of the experiment are shown in Table 6 below. *E. coli*

TABLE 6

| | Number of *coli* forms, log CFU/g | | |
|---|---|---|---|
| Water tissue | 1 month | 3 months | 6 months |
| Example 2-1 | ND | ND | ND |
| Example 2-2 | ND | ND | ND |
| Example 2-3 | ND | ND | ND |
| Example 2-4 | ND | ND | ND |
| Example 2-5 | ND | ND | ND |
| Example 2-6 | ND | ND | ND |
| Example 2-7 | ND | ND | ND |
| Example 2-8 | ND | ND | ND |
| Example 2-9 | ND | ND | ND |
| Example 2-10 | ND | ND | ND |
| Example 2-11 | ND | ND | ND |
| Example 2-12 | ND | ND | ND |
| Example 2-13 | ND | ND | ND |
| Example 2-14 | ND | ND | ND |
| Example 2-15 | ND | ND | ND |
| Example 2-16 | ND | ND | ND |
| Example 2-17 | ND | ND | ND |
| Example 2-18 | ND | ND | ND |
| Example 2-19 | ND | ND | ND |
| Example 2-20 | ND | ND | ND |
| Example 2-21 | ND | ND | ND |
| Example 2-22 | ND | ND | ND |
| Example 2-23 | ND | ND | ND |
| Example 2-24 | ND | ND | ND |
| Example 2-25 | ND | ND | ND |
| Example 2-26 | ND | ND | ND |
| Example 2-27 | ND | ND | ND |
| Example 2-28 | ND | ND | ND |
| Comp. Ex. 3-1 | ND | 0.34 | 1.32 |
| Comp. Ex. 3-2 | ND | 0.13 | 1.21 |
| Comp. Ex. 3-3 | ND | 0.12 | 1.42 |
| Comp. Ex. 3-4 | ND | 0.27 | 1.47 |
| Comp. Ex. 3-5 | ND | 0.20 | 1.64 |
| Comp. Ex. 3-6 | ND | 0.19 | 1.48 |
| Comp. Ex. 3-7 | ND | 0.18 | 1.57 |
| Comp. Ex. 3-8 | ND | 0.17 | 1.97 |
| Comp. Ex. 3-9 | ND | 0.10 | 1.69 |
| Comp. Ex. 3-10 | ND | 0.29 | 1.76 |
| Comp. Ex. 3-11 | ND | 0.28 | 1.87 |
| Comp. Ex. 3-12 | ND | 0.17 | 1.08 |
| Comp. Ex. 3-13 | ND | 0.10 | 1.75 |
| Comp. Ex. 3-14 | ND | 0.29 | 1.86 |
| Comp. Ex. 3-15 | ND | 0.28 | 1.67 |
| Comp. Ex. 3-16 | ND | 0.27 | 1.64 |
| Comp. Ex. 3-17 | ND | 0.16 | 1.45 |
| Comp. Ex. 3-18 | ND | 0.29 | 1.53 |
| Comp. Ex. 3-19 | ND | 0.28 | 1.64 |
| Comp. Ex. 3-20 | ND | 0.15 | 1.72 |
| Comp. Ex. 3-21 | ND | 0.12 | 1.32 |
| Comp. Ex. 3-22 | ND | 0.23 | 1.53 |
| Comp. Ex. 3-23 | ND | 0.24 | 1.64 |
| Comp. Ex. 3-24 | ND | 0.15 | 1.31 |
| Comp. Ex. 3-25 | ND | 0.23 | 1.46 |
| Comp. Ex. 3-26 | ND | 0.24 | 1.43 |
| Comp. Ex. 3-27 | ND | 0.17 | 1 84 |
| Comp. Ex. 3-28 | ND | 0.24 | 1.83 |
| Comp. Ex. 3-29 | ND | 0.26 | 1.94 |
| Comp. Ex. 3-30 | ND | 0.25 | 1.02 |
| Comp. Ex. 3-31 | ND | 0.14 | 1.73 |
| Comp. Ex. 3-32 | ND | 0.25 | 1.84 |
| Comp. Ex. 3-33 | ND | 1.53 | 1.15 |
| Comp. Ex. 3-34 | ND | 0.99 | 1.22 |
| Comp. Ex. 3-35 | ND | 0.19 | 1.41 |
| Comp. Ex. 3-36 | ND | 0.18 | 1.52 |
| Comp. Ex. 3-37 | ND | 1.53 | 3.15 |
| Commercially available Water tissue (Kleenex, Yuhan Kimberly Co., Ltd.) | ND | ND | ND |

* ND: Not Detected

As can be seen from the results in Table 6 above, the wet tissue of Comparative Example 3-37 containing only water did not inhibit the growth of general bacteria caused by external contamination during 6 months after manufacture, even though it was sterilized. In addition, in the case of the remaining wet tissues of Comparative Example 3, general bacteria caused by external contamination partially proliferated with the passage of time. However, in the case of the wet tissues of Example 2, it could be seen that general bacteria did not proliferate for 6 months, suggesting that the hot-water extract of *Coptidis rhizoma* according to the present invention has the effect of inhibiting external contamination without needing to add a preservative or an antibacterial agent, and thus the wet tissue containing it has high storage stability.

Meanwhile, for the wet tissues of Examples 2-1 and 2-25 to 2-28, an experiment on the degree of growth of general bacteria in the wet tissues was performed for 18 months while measurement was performed at 3-month intervals. As a result, in the wet tissue of Example 2-1, 0.3 log CFU/g or more of bacteria were detected at 15 months (not detected up to 12 months), but in the wet tissues of Examples 2-25 to 2-28, 0.3 log CFU/g or more of bacteria were detected at 18 months (not detected up to 15 months).

These results suggest that the wet tissue containing a distillate of the hot-water extract of *Coptidis rhizoma* has higher storage stability than the wet tissue containing the hot-water extract of *Coptidis rhizome*.

Example 2: Examination of Antibacterial Effect

An experiment on the antibacterial effect of the wet tissue of the present invention against *E. coli* was performed. Specifically, 70 ml of phosphate buffered saline and 5 ml of a broth of *Escherichia coli* (accession No. ATCC 25922) were placed in a 250-ml flask, and 0.75 g of each of the wet tissues of Example 2 and Comparative Example 3 was cut to small pieces (1×1 cm or less) and added thereto. Each of the flasks was shaken at 320 rpm at 25±5° C. for 1 hour. Then, each of the cultures was diluted 10-fold with phosphate buffered saline, and then 0.1 ml of each dilution was streaked on agarose medium, after which each medium was incubated at 37° C. for 24 hours. The results are shown in Table 7 below as bacteria reduction ratio relative to the wet tissue of Comparative Example 3-37.

TABLE 7

| Water tissue | Bacteria reduction ratio(%) |
| --- | --- |
| Example 2-1 | 80.5 |
| Example 2-2 | 85.8 |
| Example 2-3 | 76.5 |
| Example 2-4 | 77.6 |
| Example 2-5 | 74.4 |
| Example 2-6 | 85.5 |
| Example 2-7 | 85.6 |
| Example 2-8 | 94.7 |
| Example 2-9 | 85.9 |
| Example 2-10 | 93.0 |
| Example 2-11 | 94.7 |
| Example 2-12 | 95.8 |
| Example 2-13 | 96.3 |
| Example 2-14 | 93.4 |
| Example 2-15 | 94.5 |
| Example 2-16 | 95.2 |
| Example 2-17 | 96.3 |
| Example 2-18 | 97.4 |
| Example 2-19 | 94.5 |
| Example 2-20 | 95.3 |
| Example 2-21 | 96.4 |
| Example 2-22 | 94.5 |
| Example 2-23 | 95.6 |

TABLE 7-continued

| Water tissue | Bacteria reduction ratio(%) |
| --- | --- |
| Example 2-24 | 95.6 |
| Example 2-25 | 97.6 |
| Example 2-26 | 97.7 |
| Example 2-27 | 97.9 |
| Example 2-28 | 97.6 |
| Comp. Ex. 3-1 | 39.3 |
| Comp. Ex. 3-2 | 36.4 |
| Comp. Ex. 3-3 | 37.5 |
| Comp. Ex. 3-4 | 24.4 |
| Comp. Ex. 3-5 | 35.5 |
| Comp. Ex. 3-6 | 46.7 |
| Comp. Ex. 3-7 | 37.4 |
| Comp. Ex. 3-8 | 44.5 |
| Comp. Ex. 3-9 | 35.7 |
| Comp. Ex. 3-10 | 46.8 |
| Comp. Ex. 3-11 | 47.5 |
| Comp. Ex. 3-12 | 44.6 |
| Comp. Ex. 3-13 | 45.8 |
| Comp. Ex. 3-14 | 33.9 |
| Comp. Ex. 3-15 | 34.5 |
| Comp. Ex. 3-16 | 35.6 |
| Comp. Ex. 3-17 | 32.7 |
| Comp. Ex. 3-18 | 33.4 |
| Comp. Ex. 3-19 | 44.5 |
| Comp. Ex. 3-20 | 45.6 |
| Comp. Ex. 3-21 | 25.4 |
| Comp. Ex. 3-22 | 23.5 |
| Comp. Ex. 3-23 | 24.6 |
| Comp. Ex. 3-24 | 26.7 |
| Comp. Ex. 3-25 | 23.5 |
| Comp. Ex. 3-26 | 22.8 |
| Comp. Ex. 3-27 | 41.9 |
| Comp. Ex. 3-28 | 46.3 |
| Comp. Ex. 3-29 | 37.4 |
| Comp. Ex. 3-30 | 34.5 |
| Comp. Ex. 3-31 | 35.2 |
| Comp. Ex. 3-32 | 37.3 |
| Comp. Ex. 3-33 | 32.3 |
| Comp. Ex. 3-34 | 33.7 |
| Comp. Ex. 3-35 | 42.3 |
| Comp. Ex. 3-36 | 41.4 |
| Comp. Ex. 3-37 | 0.0 |
| commercially available Water tissue (Kleenex, Yuhan Kimberly Co., Ltd.) | 57.2 |

As can be seen from the results in Table 7 above, the medium containing the wet tissue product of the present invention showed a significant bacteria reduction ratio compared to the wet tissue of Comparative Example 3-37, suggesting that the wet tissue product of the present invention has a significantly high antibacterial activity compared to a commercially available wet tissue product. Meanwhile, the wet tissues (Comparative Examples 3-21 to 3-26) containing no *Coptidis rhizoma* extract had no antibacterial activity, suggesting that *Coptidis rhizoma* is essential for the antibacterial effect of the wet tissue of the present invention.

Experimental Example 3: Examination of Anti-Inflammatory Effect

To examine the anti-inflammatory effect of the wet tissue of the present invention, bacterial conjunctivitis patient groups, each consisting of 10 persons, were allowed to wipe their upper eyelids using one sheet of the tissue of each of Example 2 and Comparative Example 3 at 6-hour intervals. Also, for an accurate comparative experiment, Fluorometholone Ophthalmic Suspension 0.1 (based on fluorometholone) that is a bacterial conjunctivitis therapeutic agent was administered at 6-hour intervals. The therapeutic effect of the wet tissue after 2 days of use was evaluated on a five-point scale, and the results of the evaluation are shown in Table 8.

TABLE 8

| Conditions | Healing effect after 2 days of use |
| --- | --- |
| Water tissue of Example 2-1 | 3.9 |
| Water tissue of Example 2-2 | 3.8 |
| Water tissue of Example 2-4 | 3.5 |
| Water tissue of Example 2-11 | 4.9 |
| Water tissue of Example 2-12 | 4.9 |
| Water tissue of Example 2-13 | 4.7 |
| Water tissue of Example 2-25 | 4.8 |
| Water tissue of Example 2-26 | 4.8 |
| Water tissue of Comp. Ex. 3-1 | 2.0 |
| Water tissue of Comp. Ex. 3-3 | 1.8 |
| Water tissue of Comp. Ex. 3-8 | 2.2 |
| Water tissue of Comp. Ex. 3-10 | 2.1 |
| Water tissue of Comp. Ex. 3-27 | 2.3 |
| Water tissue of Comp. Ex. 3-35 | 2.2 |
| Water tissue of Comp. Ex. 3-36 | 2.0 |
| Water tissue of Comp. Ex. 3-37 | 1.1 |
| Fluorometholone Ophthalmic Suspension 0.1 | 4.8 |

5: very good,
4: good,
3: moderate,
2: poor,
1: very poor

As can be seen from the results in Table 8 above, the use of the wet tissues of Example 2 showed a therapeutic effect similar to that of the use of Fluorometholone Ophthalmic Suspension 0.1. In addition, it was shown that the wet tissues of Example 2 showed the effects of eliminating congestion, reducing inflammation, and inhibiting dry eye syndrome and pain.

Experimental Example 4: Examination of Effect on Inhibition of Oral Malodor 10 persons per group, who were in need of inhibition of oral malodor, were allowed to wipe their mouth cavity (including tongue) using one sheet of the tissue of each of Examples 2-7 and 2-10 (containing an extract prepared by extracting *Coptidis rhizoma* together with *Glycyrrhizae* radix in hot water), Comparative Examples 3-4 and 3-7, and Comparative Example 3-37 (treated with only water). The oral malodor inhibitory effect of the wet tissue after 2 days of use was evaluated on a five-point scale, and the results of the evaluation are shown in Table 9.

TABLE 9

| Conditions | Healing effect after 2 days of use |
| --- | --- |
| Water tissue of Example 2-7 | 4.1 |
| Water tissue of Example 2-10 | 4.6 |
| Water tissue of Comp. Ex. 3-4 | 2.3 |
| Water tissue of Comp. Ex. 3-7 | 2.1 |
| Water tissue of Comp. Ex. 3-37 | 1.1 |

5: very good,
4: good,
3: moderate,
2: poor,
1: very poor

As can be seen from the results in Table 9 above, the use of the wet tissues of Examples 2-7 and 2-10 (containing an extract prepared by extracting *Coptidis rhizoma* together with *Glycyrrhizae* radix in hot water under the high temperature and high pressure conditions) exhibited an excellent effect on the inhibition of oral malodor. However, the wet tissue containing only water (Comparative Example 3-37) had no effect on the inhibition of oral malodor, and the wet tissues containing an extract prepared at 100° C. and 1 atm (Comparative Examples 3-4 and 3-7) showed an insignificant effect on the inhibition of oral malodor.

Experimental Example 5: Examination of Wound Healing Effect

To examine the wound healing effect of the wet tissue of the present invention, on 10 persons per group, who had a wound having a length of 2-5 cm and a depth of 3 mm or less, the wound site was disinfected and dressed with the gauze of each of Examples 3 and 4 and Comparative Example 4. For comparison, general sterile gauze was used. After 24 hours, the gauze was replaced with fresh gauze, and after 24 hours, the degree of healing of the wound was evaluated on a five-point scale. The results of the evaluation are shown in Table below.

TABLE 10

| Conditions | wound healing effect after 2 days of use |
| --- | --- |
| gauze of Example 3 | 3.5 |
| gauze of Example 4 | 4.1 |
| Gauze of Comp. Ex. 4 | 2.5 |
| commercially available general gauze | 1.2 |

5: very good,
4: good,
3: moderate,
2: poor,
1: very poor

As can be seen from the results in Table 10 above, the wound healing effect of the gauzes of Examples 3 and 4 was significantly better than that of the general gauze of Comparative Example 4. Particularly, the wound healing effect of the gauze of Example 4 containing the distillate of hot-water extract of *Coptidis rhizoma* was significantly better than that of the gauze of Example 3 containing the hot-water extract of *Coptidis rhizome*

In addition, in the results of observation of the wound site, when the gauzes of Examples 3 and 4 were used, the wound was easily healed without forming a scab, suggesting that the gauzes showed good wound healing effects. However, the general gauze caused a severe scab, and showed little or no effect on wound healing.

Experimental Example 6: Examination of Skin Irritation of *Coptidis rhizome* Extract Using Closed Patch Test To examine the skin irritation of the hot-water extract of *Coptidis rhizoma* used in the wet tissue of the present invention, a human closed patch test was performed. This test method has been widely used to detect primary irritants. Specifically, 40 μl of each of the extracts shown in Table 11 below was applied to the back of healthy adult persons (30 men and 30 women), and then fixed to the skin using a scanpore tape. After 24 hours, the tape was detached from the skin, and after 4 hours, the results were rated. The degree of erythema and edema was rated according to the following criteria. Criteria for evaluation followed the guidelines of the International Contact Dermatitis Research Group (ICDRG) (Wooding et al, 1967; Rietschell, 1982; Fischer & Maibach, 1984; Aberer et al, 1993) as follows:

Criteria for Evaluation
0=no redness
1=mild erythema

2=intense erythema
3=intense erythema with edema
4=intense erythema with edema and vesicle

What is claimed is:

1. A method for manufacturing a wet tissue containing a *Coptidis rhizome*-containing composition (CR-composition), wherein the CR-composition is a hot-water extract of *Coptidis rhizome* or a distillate thereof; the method comprising the steps of:
    (i) mixing 100 parts by weight of *Coptidis rhizoma* with 2000-8000 parts by weight of water and extracting under a high temperature condition of 120-131° C. and a high pressure condition of 1.2-2.8 atm to prepare the hot-water extract of *Coptidis rhizome*, and optionally distilling the hot-water extract of *Coptidis rhizome* to obtain vapor, and condensing the obtained vapor, thereby preparing the distillate of the hot-water extract of *Coptidis rhizome*;
    (ii) spraying 200-400 parts by weight of the CR-composition of *Coptidis rhizoma* prepared in step (i) onto 100 parts by weight of a fabric for wet tissue to absorb the CR-composition into the fabric for wet tissue; and
    (iii) hermetically packaging and sterilizing the fabric for wet tissue absorbed with the CR-composition of *Coptidis rhizome*.

2. The method of claim 1, wherein the CR-composition is the hot-water extract.

3. The method of claim 1, wherein the CR-composition is the distillate, and the method comprises the step of distilling the hot-water extract of *Coptidis rhizome* to obtain vapor, and condensing the obtained vapor, thereby preparing the distillate of the hot-water extract of *Coptidis rhizome*.

4. A method for manufacturing an article selected from the group consisting of a cotton swab, gauze, a mask, a diaper and a sanitary napkin, the method comprising the steps of:
    (i) mixing 100 parts by weight of *Coptidis rhizoma* with 2000-8000 parts by weight of water and extracting under the high temperature and high pressure conditions of 120-131° C. and 1.2-2.8 atm to prepare a hot-water extract of *Coptidis rhizome*; and optionally distilling the hot-water extract of *Coptidis rhizome* to obtain vapor, and condensing the obtained vapor, thereby preparing a distillate of hot-water extract of *Coptidis rhizome*;
    (ii) spraying 200-400 parts by weight of a CR-composition wherein the CR-composition is the hot-water extract or the distillate thereof prepared in step (i) onto 100 parts by weight of one material selected from the group consisting of cotton, fabric for gauze, cotton fabric, natural fiber fabric, synthetic fiber fabric, mixed fiber fabric and nonwoven fabric to absorb the CR-composition into the selected material;
    (iii) drying and sterilizing the material absorbed with the CR-composition; and
    (iv) manufacturing an article selected from the group consisting of a cotton swab, gauze, a mask, a diaper and a sanitary napkin using the dried and sterilized material of step (iii), and packaging and sterilizing the manufactured article.

5. The method of claim 4, wherein the CR-composition is the hot-water extract.

6. The method of claim 4, wherein the CR-composition is the distillate, and the method comprises the step of distilling the hot-water extract of *Coptidis rhizome* to obtain vapor, and condensing the obtained vapor, thereby preparing the distillate of the hot-water extract of *Coptidis rhizome*.

* * * * *